(12) United States Patent
Suzuki et al.

(10) Patent No.: US 10,082,477 B2
(45) Date of Patent: Sep. 25, 2018

(54) RESISTIVITY-MEASURING CIRCUIT, CELL FOR MEASURING LIQUID SAMPLE, RESISTIVITY-MEASURING APPARATUS, LIQUID SAMPLE CONTROL METHOD, AND LIQUID SAMPLE CONTROL SYSTEM

(71) Applicant: HORIBA ADVANCED TECHNO, CO., LTD., Kyoto-shi, Kyoto (JP)

(72) Inventors: Riichiro Suzuki, Kyoto (JP);
Tsunetoshi Sugawara, Tokyo (JP);
Tadashi Oshio, Tokyo (JP)

(73) Assignee: HORIBA ADVANCED TECHNO, CO., LTD., Kyoto-shi, Kyoto (JP)

( * ) Notice: Subject to any disclaimer, the term of this patent is extended or adjusted under 35 U.S.C. 154(b) by 7 days.

(21) Appl. No.: 14/767,262

(22) PCT Filed: Feb. 10, 2014

(86) PCT No.: PCT/JP2014/053025
§ 371 (c)(1),
(2) Date: Aug. 11, 2015

(87) PCT Pub. No.: WO2014/126035
PCT Pub. Date: Aug. 21, 2014

(65) Prior Publication Data
US 2016/0003756 A1    Jan. 7, 2016

(30) Foreign Application Priority Data

Feb. 12, 2013  (JP) .................. 2013-024789
Feb. 12, 2013  (JP) .................. 2013-024790
Feb. 12, 2013  (JP) .................. 2013-024791

(51) Int. Cl.
*C02F 1/00*   (2006.01)
*G01N 27/07*  (2006.01)
(Continued)

(52) U.S. Cl.
CPC ............ *G01N 27/07* (2013.01); *B01D 35/02* (2013.01); *G01N 27/06* (2013.01); *G01N 27/20* (2013.01); *G01N 33/2888* (2013.01)

(58) Field of Classification Search
None
See application file for complete search history.

(56) References Cited

U.S. PATENT DOCUMENTS 3,470,465 A    9/1969   Wuschke
3,916,300 A    10/1975  Chisdes et al.
(Continued)

FOREIGN PATENT DOCUMENTS

CN    1821763 A    8/2006
CN    1928540 A    3/2007
(Continued)

OTHER PUBLICATIONS

Reverter, F. et al., "Stability and accuracy of active shielding for grounded capacitive sensors," Measurement Science and Technology, vol. 17, No. 11, Nov. 2006, Available Online Sep. 28, 2006, 7 pages.
(Continued)

*Primary Examiner* — Richard C Gurtowski
(74) *Attorney, Agent, or Firm* — Alleman Hall Creasman & Tuttle LLP

(57) ABSTRACT

The present invention is one that makes it possible to continuously measure the resistivity of a liquid sample with accuracy as well as preventing the deterioration of the liquid sample associated with measurement, such as change in quality, and relates to a resistivity-measuring circuit C that measures the resistivity in order to sense the deterioration of the liquid sample. The resistivity-measuring circuit C is one that calculates the resistivity of the liquid sample by detecting voltage generated between an outer electrode and an (Continued)

inner electrode, and between the outer electrode and the inner electrode, applies square wave AC voltage having an amplitude of 1 V to 42 V and a frequency of 0.5 Hz to 30 Hz.

8 Claims, 9 Drawing Sheets

(51) Int. Cl.
  *G01N 27/06* (2006.01)
  *G01N 33/28* (2006.01)
  *B01D 35/02* (2006.01)
  *G01N 27/20* (2006.01)

(56) References Cited

U.S. PATENT DOCUMENTS

| | | | | |
|---|---|---|---|---|
| 5,304,289 | A * | 4/1994 | Hayakawa | C02F 1/4602 205/701 |
| 2004/0089357 | A1 * | 5/2004 | Dube | B01L 3/502707 137/884 |
| 2007/0024287 | A1 | 2/2007 | Graves et al. | |
| 2010/0188111 | A1 | 7/2010 | Fougere | |

FOREIGN PATENT DOCUMENTS

| | | |
|---|---|---|
| CN | 201242533 Y | 5/2009 |
| CN | 101629925 A | 1/2010 |
| DE | 4137422 A1 | 5/1993 |
| EP | 2533036 A1 | 12/2012 |
| JP | 62010690 Y2 | 3/1987 |
| JP | 01131155 U | 9/1989 |
| JP | 02190755 A | 7/1990 |
| JP | 06058333 B2 | 8/1994 |
| JP | 06035174 Y2 | 9/1994 |
| JP | 07069246 B2 | 7/1995 |
| JP | 08014551 B2 | 2/1996 |
| JP | 11101680 A | 4/1999 |
| JP | 11281687 A | 10/1999 |
| JP | 11287776 A | 10/1999 |
| JP | 200074865 A | 3/2000 |
| JP | 2000193641 A | 7/2000 |
| JP | 2002181639 A | 6/2002 |
| JP | 2003172494 A | 6/2003 |
| JP | 2005331513 A | 12/2005 |
| JP | 3769119 B2 | 4/2006 |
| JP | 2009020063 A | 1/2009 |
| JP | 2009243304 A | 10/2009 |
| JP | 2011214954 A | 10/2011 |
| JP | 2012237558 A | 12/2012 |

OTHER PUBLICATIONS

European Patent Office, Extended European Search Report Issued in Application No. 14751757.7, dated Sep. 21, 2016, Germany, 9 pages.
Japanese Patent Office, Office Action Issued in Application No. 2013-024791, dated Dec. 26, 2013, 3 pages.
Japanese Patent Office, Office Action Issued in Application No. 2013-024791, dated Mar. 13, 2014, 3 pages.
ISA Japanese Patent Office, International Search Report Issued in Application No. PCT/JP2014/053025, dated May 20, 2014, WIPO, 4 pages.
Japanese Patent Office, Office Action Issued in Application No. 2013-024789, dated Oct. 14, 2014, 3 pages.
Japanese Patent Office, Office Action Issued in Application No. 2013-024790, dated Oct. 14, 2014, 3 pages.
Japanese Patent Office, Office Action Issued in Application No. 2013-024789, dated Jan. 15, 2015, 2 pages.
Japanese Patent Office, Office Action Issued in Application No. 2013-024790, dated Jan. 15, 2015, 2 pages.
Japanese Patent Office, Office Action Issued in Application No. 2013-014790, dated Jun. 2, 2015, 3 pages.
State Intellectual Property Office of the People's Republic of China, Office Action and Search Report Issued in Application No. 201480008366.1, dated Dec. 5, 2016, 12 pages. (Submitted with Translation of Office Action).
Mejia-Aguilar et al., "Electrical Measurement Using Voltage/Current Pulse Excitation," Proceedings of "XIX IMEKO World Congress Fundamental and Applied Metrology," Sep. 6, 2009, Lisbon, Portugal, 6 pages.
European Patent Office, Office Action Issued in Application No. 14751757.7, dated Mar. 19, 2018, Germany, 6 pages.

* cited by examiner

RESISTIVITY-MEASURING CIRCUIT, CELL FOR MEASURING LIQUID SAMPLE, RESISTIVITY-MEASURING APPARATUS, LIQUID SAMPLE CONTROL METHOD, AND LIQUID SAMPLE CONTROL SYSTEM

TECHNICAL FIELD

The present invention relates to a resistivity-measuring apparatus that measures the resistivity of a liquid sample such as lubricating oil, a resistivity-measuring circuit and a cell for measuring a liquid sample that are used for the resistivity-measuring apparatus, and a liquid sample control method and a liquid sample control system that use the resistivity-measuring apparatus.

BACKGROUND ART

As an apparatus for measuring the resistivity of IPA (isopropyl alcohol), which is insulating liquid, one disclosed in Patent Literature 1 has been contrived. The resistivity-measuring apparatus is one that measures the resistivity of IPA positioned between an outer electrode and an inner electrode by applying AC voltage between the outer electrode and the inner electrode.

In Patent Literature 1, the resistivity of IPA is approximately 1000 MΩ·cm, and as the AC voltage applied between the outer electrode and the inner electrode, AC voltage having an amplitude of approximately 2 V and a frequency of 100 Hz is used. Note that the resistivity of pure water or the like in addition to IPA is also generally measured using similar AC voltage.

On the other hand, to measure the resistivity of oil such as lubricating oil in order to sense the deterioration of the oil, using the above-described resistivity-measuring apparatus is considered.

However, since the resistivity of oil is several tens times to several hundred times higher as compared with the resistivity of IPA, current flowing through a measuring circuit having the outer electrode and the inner electrode is small, making the measurement difficult, and also floating capacitance of the measuring circuit deteriorates AC voltage responsiveness. As a result, in the case of applying the AC voltage having a frequency of 100 Hz, before a signal (e.g., output voltage) outputted from the measuring circuit stabilizes, the polarity of the AC voltage is switched, thus giving rise to the problem of being unable to accurately measure the resistivity of oil.

Also, a possible way to measure the resistivity of oil is to set voltage applied between the outer electrode and the inner electrode to a high voltage such as 1000 V to increase detected current. Note that to measure the resistivity of oil, high voltage has been generally applied in the past.

However, in the case of applying a high voltage of, for example, 1000 V to oil, the oil is oxidized and changed in quality, i.e., there is the problem that the measurement causes the deterioration of the oil.

CITATION LIST

Patent Literature a. Patent Literature 1: Japanese Patent No. 3769119

SUMMARY OF INVENTION

Technical Problem

Therefore, the present invention is made in order to solve the above-described problems at once, and a main intended object thereof is to make it possible to continuously measure the resistivity of a liquid sample with accuracy as well as preventing the deterioration of the liquid sample, such as change in quality, associated with measurement.

Solution to Problem

That is, a resistivity-measuring circuit according to the present invention is a resistivity-measuring circuit that measures resistivity in order to sense the deterioration of a liquid sample, and the resistivity-measuring circuit is one that measures the resistivity of the liquid sample between a pair of electrodes by detecting voltage generated between the pair of electrodes, and between the pair of electrodes, applies square wave AC voltage having an amplitude of 1 V to 42 V and a frequency of 0.5 Hz to 30 Hz. Note that liquid samples include lubricating oils, liquid organic media for lubrication, rust preventing oils, electric discharge machining oils, fluid-pressure operating medium liquids, oils such as cooking oils, heat medium liquids, heat treatment liquids, hydrocarbon system solvents for diluting varnishes, pigments, agrichemicals, and the like, hydrocarbon system solvents for cleaning, greases having fluidity, alcohols such as IPA (isopropyl alcohol), and the like.

In such a configuration, since the square wave AC voltage as described above is applied, the formation of electric double layers at the boundaries between the electrodes and the liquid sample can be suppressed to continuously measure the resistivity of the liquid sample. Also, since the voltage of 1 V to 42 V is applied, the deterioration of the liquid sample during the measurement, such as change in quality, can be prevented. Note that since the AC voltage is set within the range from 1 V to 42 V, a power supply can be configured at low cost, and also even in case of electric shock, a risk to a human body can be reduced. Further, since the frequency is within the range from 0.5 Hz to 30 Hz, a signal outputted from the measuring circuit can be stabilized before switching the polarity of the AC voltage, and therefore the resistivity of the liquid sample can be accurately measured to accurately sense the deterioration of the liquid sample. A cell for measuring the liquid sample makes it possible to not only measure the resistivity of a liquid sample having resistivity several tens times to several hundred times higher as compared with the resistivity of IPA, such as oil, but also obviously measure the resistivity of a liquid sample having resistivity less than 10 GΩ·cm, such as IPA.

Note that in the case of applying DC voltage between the outer electrode and the inner electrode, charges accumulate in electric double layers at the boundaries between the electrodes and the liquid sample, and as the potential of each of the electric double layers gradually increases, a potential gradient between the electrodes decreases to decrease ion mobility, thus increasing resistivity. For this reason, in the case of using DC voltage for continuously measuring the resistivity of the liquid sample, it is difficult to accurately measure the resistivity of the liquid sample.

It is desirable to have a shield drive circuit using an operational amplifier, which zeroes a potential difference of floating capacitance formed between wiring lines respectively connected to the pair of electrodes. In doing so, the floating capacitance formed between the wiring lines respectively connected to the pair of electrodes can be separated from the measuring circuit to quicken a response of the signal indicating the resistivity of the liquid sample as well as easily extracting the signal. As a result, the resistivity of the liquid sample can be accurately measured to accurately sense the deterioration of the liquid sample.

Also, the resistivity of IPA is less than 10 GΩ·cm, and a cell constant defined by the outer electrode and the inner electrode is 0.01/cm or more. Given that the opposite area between the inner surface of the outer electrode and the outer surface of the inner electrode is S ($cm^2$), and the opposite distance between the inner surface of the outer electrode and the outer surface of the inner electrode is L (cm), the cell constant has a value expressed by L/S.

Further, since the resistivity of oil is several tens times to several hundred times higher as compared with the resistivity of IPA, the cell constant (0.01/cm) of the resistivity-measuring apparatus may cause the resistivity of oil to exceed a measurement range. For this reason, it is necessary to widen the measurement range by decreasing the cell constant defined by the outer electrode and the inner electrode.

A conventional cell structure is a single-sided support structure that holds one axial direction end part of a columnar inner electrode using an insulating member with the inner electrode inserted into a cylindrical outer electrode. In order to decrease a cell constant (S/L) of such a cell structure, it is possible to decrease the opposite distance between the inner surface of the outer electrode and the outer surface of the inner electrode. Alternatively, it is possible to increase the opposite area between the inner surface of the outer electrode and the outer surface of the inner electrode, i.e., to increase the length dimensions of the outer electrode and the inner electrode, or to take another measure.

However, in the case of, as the cell structure based on the single-sided support structure, employing a structure adapted to decrease the opposite distance between the inner surface of the outer electrode and the outer surface of the inner electrode, or increase the length dimensions of the outer electrode and the inner electrode, a free end of the inner electrode is easily shifted by external vibration, and as a result, the inner electrode and the outer electrode contact with each other to make measurement impossible, or the opposite distance between the outer surface of the inner electrode and the inner surface of the outer electrode is changed to cause a measurement error.

Therefore, the present invention intends to decrease a cell constant of a liquid sample measuring cell as well as reducing an axial shift of an inner electrode by vibration to improve measurement accuracy.

That is, the liquid sample measuring cell according to the present invention is a liquid sample measuring cell for measuring the resistivity of a liquid sample, and includes: a cylindrical outer electrode; a columnar inner electrode that is inserted into the outer electrode and provided coaxially with the outer electrode; and insulating members that fix the inner electrode with respect to the outer electrode at both axial direction end parts, and fix the opposite distance between the inner surface of the outer electrode and the outer surface of the inner electrode to thereby form a measurement space. Note that liquid samples include lubricating oils, liquid organic media for lubrication, rust preventing oils, electric discharge machining oils, fluid-pressure operating medium liquids, oils such as cooking oils, heat medium liquids, heat treatment liquids, hydrocarbon system solvents for diluting varnishes, pigments, agrichemicals, and the like, hydrocarbon system solvents for cleaning, greases having fluidity, alcohols such as IPA (isopropyl alcohol), and the like.

Since such a liquid sample measuring cell is a so-called double-sided support structure that at the both axial direction end parts, fixes the inner electrode with respect to the outer electrode using the insulating members, and the insulating members fix the opposite distance between the inner surface of the outer electrode and the outer surface of the inner electrode, the inner electrode can be prevented from being easily shifted by external vibration with respect to the outer electrode, and thereby a variation in opposite distance can be suppressed. This makes it possible to prevent being unmeasurable by vibration to reduce a measurement error despite decreasing a cell constant by employing a structure adapted to decrease the opposite distance between the inner surface of the outer electrode and the outer surface of the inner electrode or a structure adapted to increase the length dimensions of the outer electrode and the inner electrode. Accordingly, measurement accuracy of the resistivity of the liquid sample can be improved to accurately sense the deterioration of the liquid sample. The liquid sample measuring cell makes it possible to not only measure the resistivity of a liquid sample having resistivity several tens times to several hundred times higher as compared with the resistivity of IPA, such as oil, but also obviously measure the resistivity of a liquid sample having resistivity less than 10 GΩ·cm, such as IPA.

The insulating members close the openings of the outer electrode at the both axial direction end parts to thereby close both axial direction end parts of the measurement space, and it is desirable that in the inner electrode or an insulating member in one axial direction end part, a liquid sample introduction path for introducing the liquid sample into the measurement space is formed, and in the inner electrode or an insulating member in the other axial direction end part, a liquid sample lead-out path for leading out the liquid sample from the measurement space is formed. In such a configuration, since the liquid sample introduction path and the liquid sample lead-out path are formed in the inner electrode or the insulating members, it is not necessary to provide the outer electrode with an introduction port and a lead-out port, and therefore the opposite area between the outer electrode and the inner electrode can be increased. On the other hand, in the case of forming an introduction port and a lead-out port in the outer electrode, each of the introduction port and the lead-out port is provided in one position from the perspective of increasing the opposite area; however, if so, each of the numbers of liquid sample inlets and liquid sample outlets will be one, and therefore the liquid sample is easily retained to easily accumulate air bubbles.

It is desirable that the liquid sample introduction path is one having multiple liquid sample inlets communicatively connected to the measurement space, and the liquid sample lead-out path is one having multiple liquid sample outlets communicatively connected to the measurement space. In such a configuration, since the liquid sample introduction path has the multiple liquid sample inlets, the liquid sample can be uniformly spread in a circumferential direction of the measurement space. Also, since the liquid sample lead-out path has the multiple liquid sample outlets, retention of the liquid sample in the measurement space can be prevented to efficiently lead out the liquid sample.

It is desirable that the multiple liquid sample inlets and the multiple liquid sample outlets are formed in the circumferential direction of the measurement space at regular intervals. In doing so, the measurement space can be uniformly filled with the liquid sample, and also the liquid sample can be uniformly discharged from the measurement space in the circumferential direction to further prevent air bubbles from being accumulated.

It is desirable that the liquid sample inlets are formed at the lowermost end of the measurement space, and the liquid sample outlets are formed at the uppermost end of the measurement space. In doing so, dead spaces in the lower end part and upper end part of the measurement space can be made as small as possible to prevent air bubbles from being accumulated.

Also, lubricating oil used for, for example, bearings becomes depolymerized or oxidized as the oil is used, and thereby friction performance is deteriorated to increase the abrasion of a bearing. For this reason, in order to roughly estimate the time to exchange or replenish the lubricating oil, the resistivity of the lubricating oil is measured to determine the deterioration of the lubricating oil.

As a conventional resistivity-measuring apparatus, a possible one is a measuring instrument that is fixed to the outer ring of a rolling bearing, and performs measurement by compensating the volume resistivity, dielectric constant, or dielectric tangent of lubricating oil inside the rolling bearing in terms of temperature.

However, although the measuring instrument that compensates the volume resistivity or the like obtained thereby in terms of temperature as described above can be applied in the case where the volume resistivity or the like of the lubricating oil is within a measurement range of the measuring instrument, in the case where the volume resistivity or the like of the lubricating oil is out of the measurement range, the measuring instrument has the problem of being unable to perform temperature compensation.

In particular, the volume resistivity or the like of the lubricating oil is different depending on the temperature of the lubricating oil, and therefore in some cases, depending on the temperature of the lubricating oil, the volume resistivity or the like of the lubricating oil cannot be measured.

Also, depending on the type of lubricating oil, the deterioration degree of lubricating oil is different, and volume resistivity is different depending on the deterioration degree, so that in some cases, depending on the deterioration degree of lubricating oil, measurement cannot be performed. That is, the resistivity of lubricating oil before use is higher than that of the lubricating oil in use or after use, and therefore the resistivity of new lubricating oil may be out of a measurement range.

Further, there are problems such as the problem that even in the case where both resistivities of some lubricating oil before use and after use are within a measurement range and therefore measurable, in the case of measuring another type of lubricating oil, resistivity before use is out of the measurement range, and in order to measure that type of lubricating oil, it is necessary to use a measuring instrument having another measurement range.

Therefore, the present invention intends to, in order to obtain a temperature suitable to measure the resistivity of each of liquid samples such as various oils, control the temperature of that liquid sample to be constant, thus making it possible to measure resistivities of the various liquid samples, as well as without necessarily relying on temperature compensation, reducing a measurement error associated with a variation in temperature of the liquid sample.

That is, a resistivity-measuring apparatus according to the present invention is a resistivity-measuring apparatus that measures the resistivity of a liquid sample, and includes: a liquid sample measuring cell in which a columnar inner electrode is arranged inside a tubular outer electrode, and between the electrodes, a cell space is formed; a heater that heats the liquid sample contained in the cell space; a resistivity measuring part that measures the resistivity of the liquid sample by detecting voltage generated between the outer electrode and the inner electrode; a heating temperature setting signal reception part that receives a heating temperature setting signal indicating a heating temperature for the liquid sample; and a heater control part that controls the heater on the basis of the heating temperature setting signal. Note that liquid samples include lubricating oils, liquid organic media for lubrication, rust preventing oils, electric discharge machining oils, fluid-pressure operating medium liquids, oils such as cooking oils, heat medium liquids, heat treatment liquids, hydrocarbon system solvents for diluting varnishes, pigments, agrichemicals, and the like, hydrocarbon system solvents for cleaning, greases having fluidity, alcohols such as IPA (isopropyl alcohol), and the like.

In such a configuration, since the temperature of the liquid sample contained in the cell space is regulated to the predetermined heating temperature, a temperature suitable to measure the resistivity of each of various liquid samples can be obtained, and therefore resistivities of the various liquid samples can be measured. Also, since the liquid sample contained in the cell space is controlled to be constant, without necessarily relying on temperature compensation, a measurement error associated with a variation in temperature of the liquid sample can be reduced to accurately measure the resistivity of the liquid sample. Accordingly, the deterioration of various liquid samples can be accurately sensed. Further, in the case of a liquid sample having particularly high viscosity, the viscosity is decreased by heating, and therefore the liquid sample can be made to easily circulate through the liquid sample measuring cell.

Also, a resistivity-measuring apparatus according to the present invention includes: a data storage part that stores heating temperature setting data indicating a heating temperature set for each type of a liquid sample; and a liquid sample selection signal reception part that receives a liquid sample selection signal indicating the type of the liquid sample contained in the liquid sample measuring cell, in which the heater control part controls the heater on the basis of the heating temperature setting data and a heating temperature setting signal obtained from the liquid sample selection signal.

In such a configuration, since a user only inputs the type of a liquid sample, and thereby temperature can be regulated to a temperature suitable to measure the resistivity of the liquid sample, a temperature suitable to measure the resistivity of each of various liquid samples can be obtained, and therefore resistivities of the various liquid samples can be measured. Also, since the temperature of a liquid sample contained in the cell space is controlled to be constant, a measurement error associated with a variation in temperature of the liquid sample can be reduced without necessarily relying on temperature compensation, and therefore the resistivity of the liquid sample can be accurately measured. Accordingly, the deterioration of various liquid samples can be accurately sensed. Further, in the case of a liquid sample having particularly high viscosity, the viscosity is decreased by heating, and therefore the oil can be made to easily circulate through the liquid sample measuring cell.

It is desirable that the heater is provided on a part of the outer circumferential surface of the outer electrode. In such a configuration, since the heater is provided on the part of the outer circumferential surface of the outer electrode, in the case of cooling the outer electrode, heat dissipation can be facilitated from an area where the heater is not provided, and therefore the outer electrode can be preferably cooled.

It is desirable that the heater is provided on a part of the outer circumferential surface of the outer electrode in a circumferential direction, and a temperature sensor adapted to detect the temperature of the outer electrode is provided on a part of the outer circumferential surface of the outer electrode where the heater is not provided. In doing so, the heater and the temperature sensor can be independently replaced such as being attached or detached.

Advantageous Effects of Invention

According to the present invention configured as described, the resistivity of a liquid sample can be continuously measured with accuracy while preventing the deterioration of the liquid sample, such as change in quality, associated with measurement.

REFERENCE SIGNS LIST

100 Resistivity-measuring apparatus
2 Oil measuring cell (liquid sample measuring cell)
21 Outer electrode
22 Inner electrode
4 Resistivity measuring part
C Resistivity-measuring circuit
Ca Reference resistance
Cb AC power supply
OP Operational amplifier
CL1 Wiring line connected to outer electrode
CL2 Wiring line connected to inner electrode
C1 Shield drive circuit
Cd Floating capacitance

DESCRIPTION OF EMBODIMENTS

One embodiment of a resistivity-measuring apparatus according to the present invention is described below with reference to drawings.

A resistivity-measuring apparatus 100 according to the present embodiment is one that in order to sense the deterioration of lubricating oil used for bearings, gears, and the like, or hydraulic oil used for hydraulic systems and the like (hereinafter simply referred to as oil), continuously measures the resistivity (electrical resistivity) of the oil (liquid sample).

Figure 1:
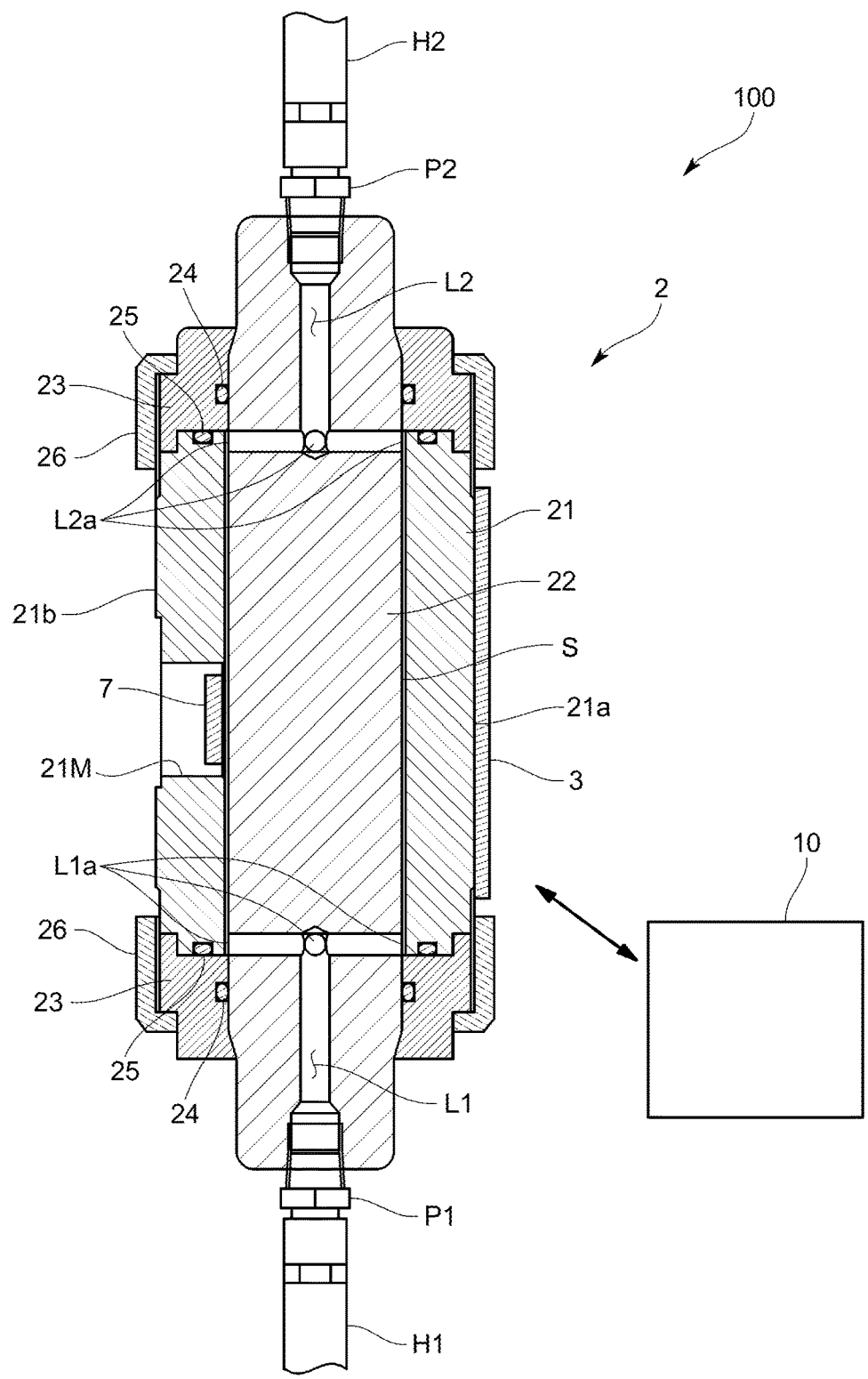
FIG. 1 is a vertical cross-sectional view of an oil measuring cell according to one embodiment of the present invention.
Figure 2:
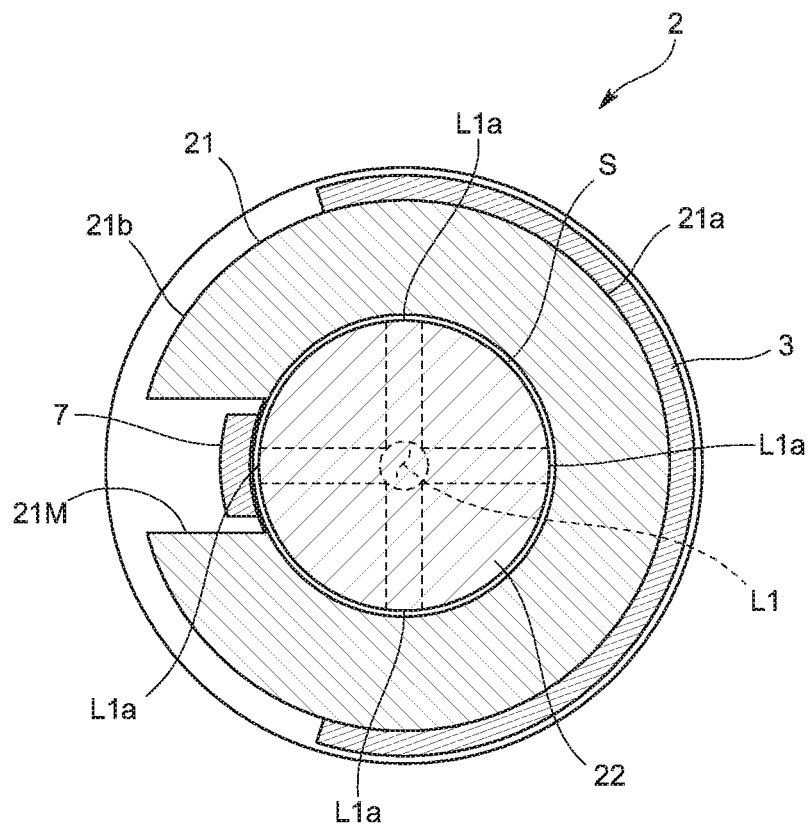
FIG. 2 is a horizontal cross-sectional view of the oil measuring cell in the same embodiment.
Figure 3:
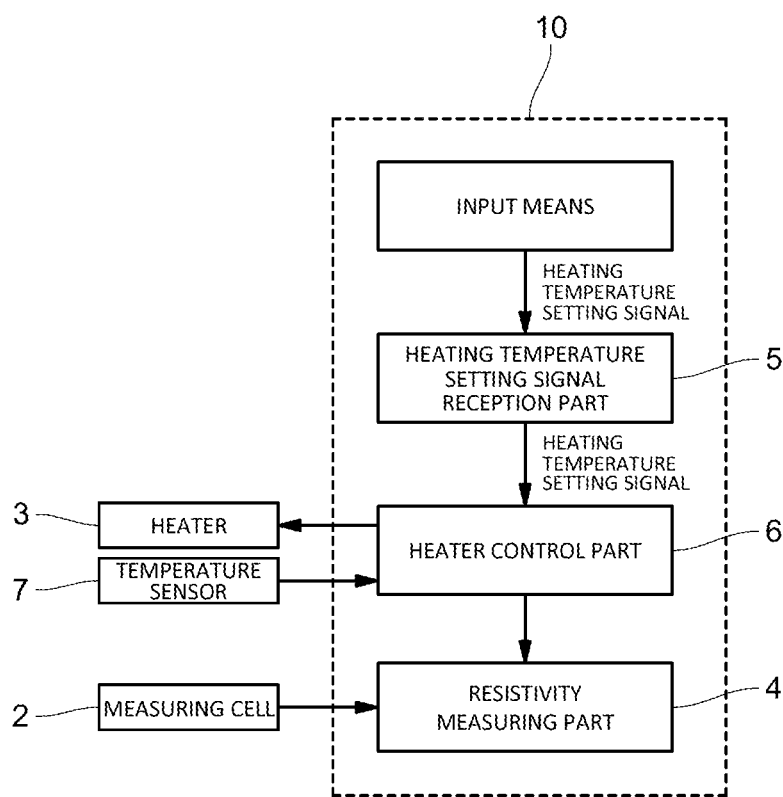
FIG. 3 is a functional configuration diagram of a control device of a resistivity-measuring apparatus in the same embodiment.

Specifically, the resistivity-measuring apparatus 100 is an apparatus of a dual electrode type, and as illustrated in FIGS. 1 to 3, includes: an oil measuring cell (corresponding to a liquid sample measuring cell of the present invention) 2 in which inside a cylindrical outer electrode 21, a columnar inner electrode 22 is arranged, and between the electrodes 21 and 22, a cell space S is formed; a heater 3 that is provided on the outer electrode 21 and heats oil contained in the cell space S; a resistivity measuring part 4 that measures the resistivity of the oil by detecting voltage generated between the outer electrode 21 and the inner electrode 22; a heating temperature setting signal reception part 5 that receives a heating temperature setting signal indicating a heating temperature for the oil; and a heater control part 6 that controls the heater 3 on the basis of the heating temperature setting signal. Note that in the present embodiment, the resistivity measuring part 4, the heating temperature setting signal reception part 5, and the heater control part 6 are included in a control device 10. In the following, the respective parts are described.

As illustrated in FIGS. 1 and 2, the oil measuring cell 2 includes: the cylindrical outer electrode 21; the columnar inner electrode 22 that is inserted into the outer electrode 21 and provided coaxially with the outer electrode 21; and insulating members 23 that fix the outer electrode 21 and the inner electrode 22 to each other and close both end openings of the outer electrode 21 to, between the inner surface of the outer electrode 21 and the outer surface of the inner electrode 22, form the cell space S adapted to contain the oil.

More specifically, the oil measuring cell 2 includes the insulating members 23 that form the oil measurement space (cell space) S by fixing the inner electrode 22 with respect to the outer electrode 21 at both axial direction end parts, and fixing the opposite distance between the inner surface of the outer electrode 21 and the outer surface of the inner electrode 22.

The outer electrode 21 and the inner electrode 22 in the present embodiment are formed of stainless steel.

The insulating members 23 are ones that suppress vibration of the inner electrode 22 due to external vibration by fixing the inner electrode 22 with respect to the outer electrode 21 on the basis of the double-sided support structure. Also, the insulating members 23 are ones that close the both end openings of the outer electrode 21 to, between the inner surface of the outer electrode 21 and the outer surface of the inner electrode 22, form the cell space S adapted to contain the oil. The insulating members 23 close the both axial direction end parts of the cell space S to form the cell space S as a substantially cylindrical space.

Further, the insulating members 23 are annularly shaped members, of which opening parts are inserted with the axial direction end parts of the inner electrode 22 via sealing members 24 such as O-rings and the axial direction end surfaces are brought into close contact with axial direction end surfaces of the outer electrode 21 via sealing member 25 such as O-rings, respectively. The insulating members 23 are fixed to the outer electrode 21 by annularly shaped fixing members 26, respectively. Since as described, the outer electrode 21 and the inner electrode 22 are fixed by the insulating members 23 at the both axial direction end parts, thus being resistant to vibration, a variation in opposite direction (gap) between the inner surface of the outer electrode 21 and the outer surface of the inner electrode 22 can be suppressed, and therefore the gap between the inner surface of the outer electrode 21 and the outer surface of the inner electrode 22 can be decreased to decrease a cell constant to approximately 1/10 of a conventional one. In the present embodiment, the cell constant of the oil measuring cell 2 can be, for example, 0.001/cm.

Also, in the oil measuring cell 2, an oil introduction path L1 for introducing the oil into the cell space S is formed in the inner electrode 22 on one axial direction end side, whereas in the inner electrode 22 on the other axial direction end side, an oil lead-out path L2 for leading out the oil from the cell space S is formed. An introduction port P1 of the oil introduction path L1 and a lead-out port P2 of the oil lead-out path L2 are respectively connected with external pipes H1 and H2 made of an insulating material such as PFA. By configuring the external pipes H1 and H2 as insulating pipes as described, insulation from the outside can be ensured to reduce noise current, and thereby measurement can be stably performed. The external pipes H1 and H2 are connected to bearings, gears, hydraulic system, or the like directly or via other connecting pipes. Note that the external pipe H1 is provided with an unillustrated flowmeter.

The oil introduction path L1 is formed in one axial direction end part of the inner electrode 22, and has multiple oil inlets L1a via which the oil introduction path L1 is communicatively connected to one axial direction end part of the cell space S. On the other hand, the oil lead-out path L2 is formed in the other axial direction end part of the inner electrode 22, and has multiple oil outlets L2a via which the oil lead-out path L2 is communicatively connected to the other axial direction end part of the cell space S. Note that the one and other axial direction end parts of the inner electrode 22 refer to parts extending to the outer sides of the outer electrode 21, or parts near the parts. Since the oil introduction path L1 and the oil lead-out path L2 are formed in the insulating members 23 as described, it is not necessary to provide the outer electrode 21 or the inner electrode 22 with the introduction port P1 and the lead-out port P2, and therefore the opposite area between the outer electrode 21 and the inner electrode 22 can be increased to decrease the cell constant. Also, since the oil introduction path L1 has the multiple oil inlets L1a, the oil can be uniformly spread in a circumferential direction in the cell space S, and also since the oil lead-out path L2 has the multiple oil outlets L2a, retention of the oil inside the cell space S can be prevented to efficiently lead out the oil. Accordingly, the resistivity of the oil can be accurately measured.

Also, in the oil measuring cell 2 in the present embodiment, the oil inlets L1a are formed at the lowermost end of the cell space S, and the oil outlets L2a are formed at the uppermost end of the cell space S. That is, the oil inlets L1a are opened in the lower edge part of the outer surface of the inner electrode 22 forming the cell space S. On the other hand, the oil outlets L2a are opened in the upper edge part of the outer surface of the inner electrode 22 forming the cell space S. In doing so, dead spaces in the lower end part and upper end part of the cell space S can be made as small as possible to prevent air bubbles from being accumulated. In addition, the above configuration makes it possible to increase the opposite area between the outer electrode 21 and the inner electrode 22 to decrease the cell constant. Further, the multiple oil inlets L1a and the multiple oil outlets L2a are formed in the circumferential direction of the cell space S at regular intervals. The cell space S can be uniformly filled with the oil, and also the oil can be uniformly discharged from the cell space S in the circumferential direction to further prevent air bubbles from being accumulated.

Further, in the oil measuring cell 2 in the present embodiment, on part of the outer circumferential surface 21a of the outer electrode 21, the heater 3 for heating the oil contained in the cell space S is provided. The heater 3 is, for example, a sheet-like one configured to incorporate a heating resistor in a flexible member such as silicon. Also, the heater 3 is provided in close contact with the outer circumferential surface 21a of the outer electrode 21. Specifically, the heater 3 is provided corresponding to substantially the whole of the inner cell space S in the axial direction, and in the circumferential direction, provided on the part of the outer circumferential surface 21a such that the other part is exposed to the outside. The outside exposed part 21b functions as a heat dissipation part. Note that since the outer electrode 21 is formed of stainless steel and superior in thermal conductivity, the heater 3 partially provided can heat the whole of the cell space S, and the outside exposed part 21b can easily cool the cell space S as well. In addition, the heater 3 is controlled in terms of flowing current by the below-described heater control part 6 of the control device 10.

Also, the part of the outer circumferential surface 21a of the outer electrode 21 where the heater 3 is not provided, i.e., the outside exposed part 21b is provided with a temperature sensor 7 adapted to detect the temperature of the outer electrode 21. Note that the temperature sensor 7 is provided on the bottom surface of a concave part 21M formed in the outside exposed part 21b. In doing so, the temperature of the outer electrode 21 can be accurately detected. In addition, in consideration of vertical symmetry of the outer electrode 21, the temperature sensor 7 is provided in the axial direction center part of the outer electrode 21. A detection signal obtained by the temperature sensor 7 is acquired by the control device 10.

The control device 10 is one that controls the heater 3 to make the temperature of the outer electrode 21 constant using detected temperature by the temperature sensor 7 as well as measuring the resistivity of the oil flowing through the oil measuring cell 2. Specifically, the control device 10 functions as the resistivity measuring part 4, heating temperature setting signal reception part 5, heater control part 6, and the like. In addition, the control device 10 is one that is configured to include a digital or analog electric circuit having a CPU, a memory, an A/D converter, a D/A converter, and the like, and may be a dedicated one or one adapted to partially or wholly use a general-purpose computer such as a personal computer. Alternatively, the control device 10 may be configured to, without using the CPU, function as the above-described respective parts only using an analog circuit, or is not required to be physically integrated one but may be one including multiple devices mutually connected by wire or wireless.

The resistivity measuring part 4 is one that measures the resistivity of the oil by detecting voltage generated between the outer electrode 21 and the inner electrode 22.

Figure 4:
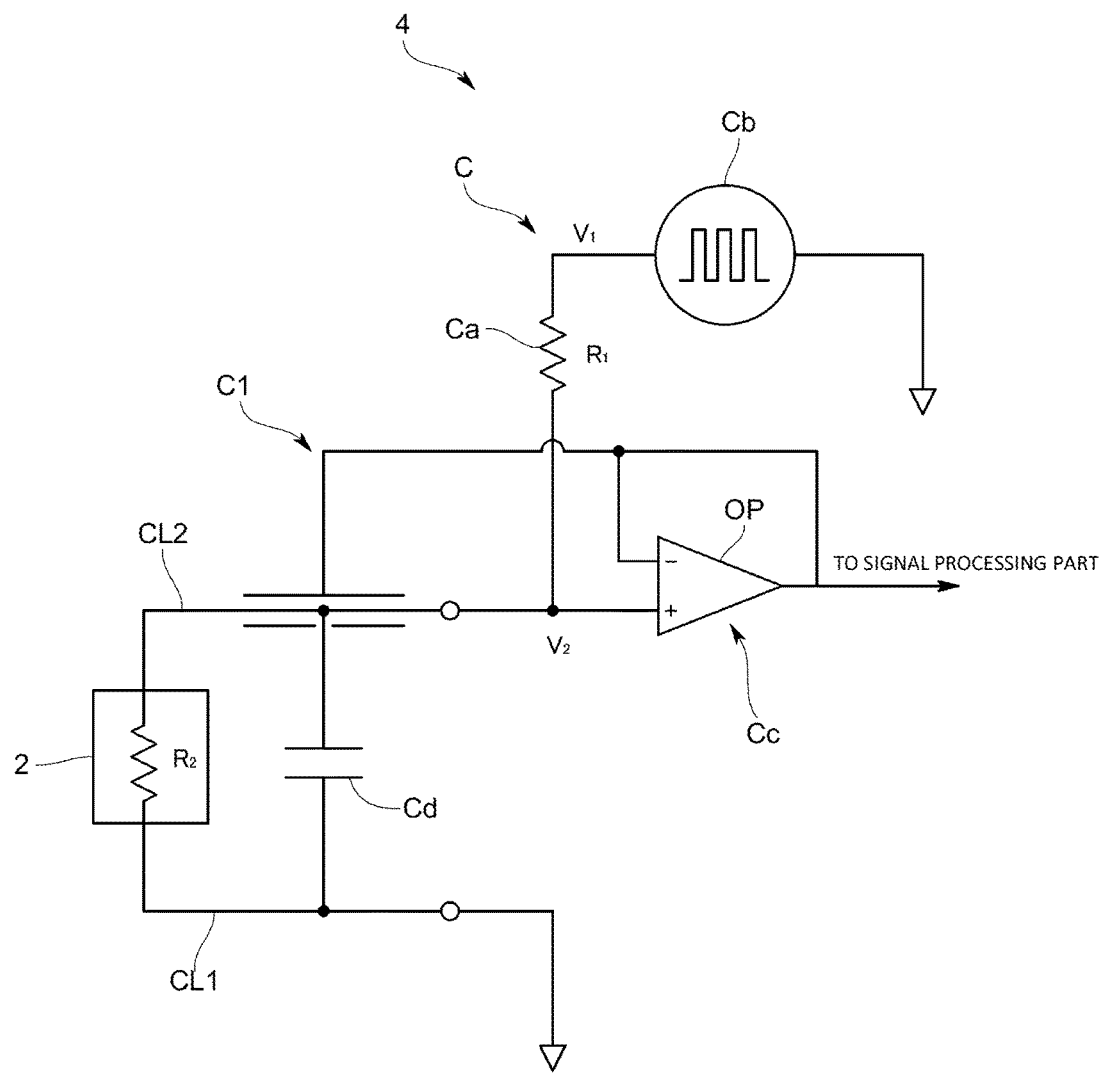
FIG. 4 is a schematic diagram illustrating a resistivity-measuring circuit in the same embodiment.

Specifically, the resistivity measuring part 4 is one having a resistivity-measuring circuit C illustrated in FIG. 4. The resistivity-measuring circuit C has: a reference resistor Ca ($R_1$) that is connected to the inner electrode 22 in series and has a known resistance value; an AC power supply Cb that applies AC voltage ($V_1$) between the pair of electrodes 21 and 22 and to the reference resistor Ca; a detection part Cc that detects the inter-electrode voltage ($V_2$) generated between the pair of electrodes 21 and 22; and a signal processing part (not illustrated) that uses output voltage from the detection part Cc to calculate the resistivity ($R_2$) of the oil. The detection part Cc in the present embodiment is configured to include an operational amplifier OP that performs impedance conversion of the inter-electrode voltage ($V_2$) to give the output. Also, for the calculation of the resistivity ($R_2$) by the signal processing part, the expression $V_2/R_2=V_1/(R_1+R_2)$ is used.

Further, the AC power supply Cb is one that between the outer electrode 21 and the inner electrode 22, applies the AC voltage ($V_1$) of a square wave having an amplitude within the range from 1 V to 42 V and a frequency within the range from 0.5 Hz to 30 Hz. Note that in order to ensure response speed, the frequency of the square wave AC voltage is preferably 2 Hz or more, and in order to ensure measurement accuracy, preferably 15 Hz or less. Also, the amplitude of the square wave AC voltage is preferably 15 V or less because of the use of existing circuit elements. The signal processing part is configured to, at the timing when the output voltage outputted from the detection part Cc is stabilized in association with the application of the square wave AV voltage ($V_1$) by the AC power supply Cb, calculate the resistivity using the stabilized output voltage. Note that as the configuration of the signal processing part adapted to calculate the resistivity using the stabilized output voltage, (1) a configuration adapted to calculate the resistivity using output voltage in the latter half part of the square wave, i.e., output voltage acquired after a predetermined time has passed since the polarity of the AC voltage was switched (in other words, just before the polarity of the AC voltage is switched), (2) a configuration adapted to determine whether or not output voltage is stabilized by calculating a variation in output voltage, and in the case where it is determined that the output voltage is stabilized, calculate the resistivity using the output voltage, or the like is possible.

Also, the resistivity-measuring circuit C includes a shield drive circuit C1 that zeros a potential difference of floating capacitance Cd formed between a wiring line CL1 connected to the outer electrode 21 and a wiring line CL2 connected to the inner electrode 22. The shield drive circuit C1 is configured using the operational amplifier OP included in the detection part Cc. In doing so, charging/discharging current to/from the floating capacitance Cd formed between the wiring line CL1 connected to the outer electrode 21 and the wiring line CL2 connected to the inner electrode 22 can be decreased to easily extract an electrical signal indicating true resistivity. Also, a time constant of the resistivity-measuring circuit C can be decreased to shorten a time required for the inter-electrode voltage ($V_2$) to stabilize. As a result, the resistivity of the oil can be accurately measured to accurately sense the deterioration of the oil.

Further, the AC power supply Cb is one that between the outer electrode 21 and the inner electrode 22, applies the square wave AC voltage ($V_1$) having the predetermined amplitude and the predetermined frequency that makes it possible to continuously measure the resistivity of the oil and prevent the deterioration of the oil by the measurement. If so, since the square wave AC voltage is applied, the formation of electric double layers at the boundaries between the electrodes 21 and 22 and the oil can be suppressed to continuously measure the resistivity of the oil. Also, since the voltage having the predetermined amplitude is applied, deterioration by measurement, such as change in quality during the measurement, can be prevented.

Also, the signal processing part is configured to, at the timing when the output voltage outputted from the detection part Cc is stabilized in association with the application of the square wave AV voltage ($V_1$) by the AC power supply Cb, calculate the resistivity using the stabilized output voltage. Note that as the configuration of the signal processing part adapted to calculate the resistivity using the stabilized output voltage, (1) a configuration adapted to calculate the resistivity using output voltage in the latter half part of the square wave, i.e., output voltage acquired after a predetermined time has passed since the polarity of the AC voltage was switched (in other words, just before the polarity of the AC voltage is switched), (2) a configuration adapted to determine whether or not output voltage is stabilized by calculating a variation in output voltage, and in the case where it is determined that the output voltage is stabilized, calculate the resistivity using the output voltage, or the like is possible.

Figure 5:
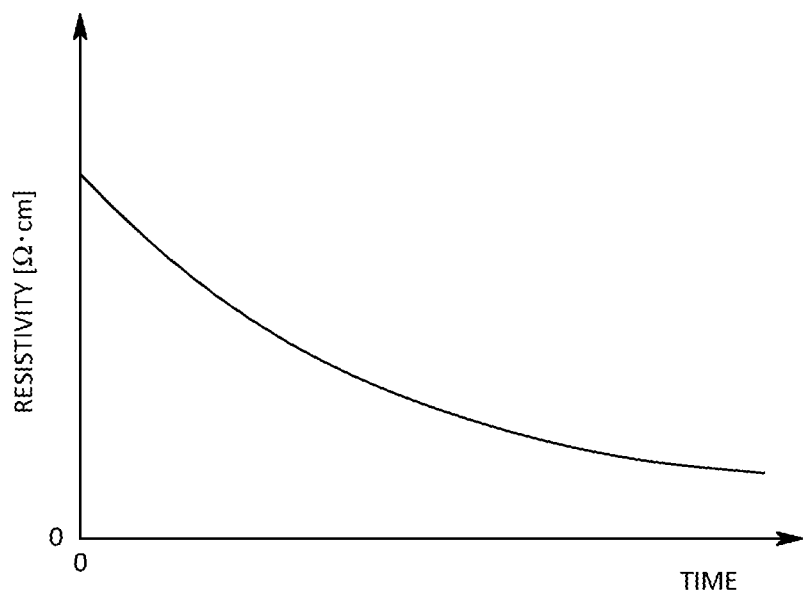
FIG. 5 is a schematic diagram illustrating a time dependent change in resistivity of oil.
Figure 6:
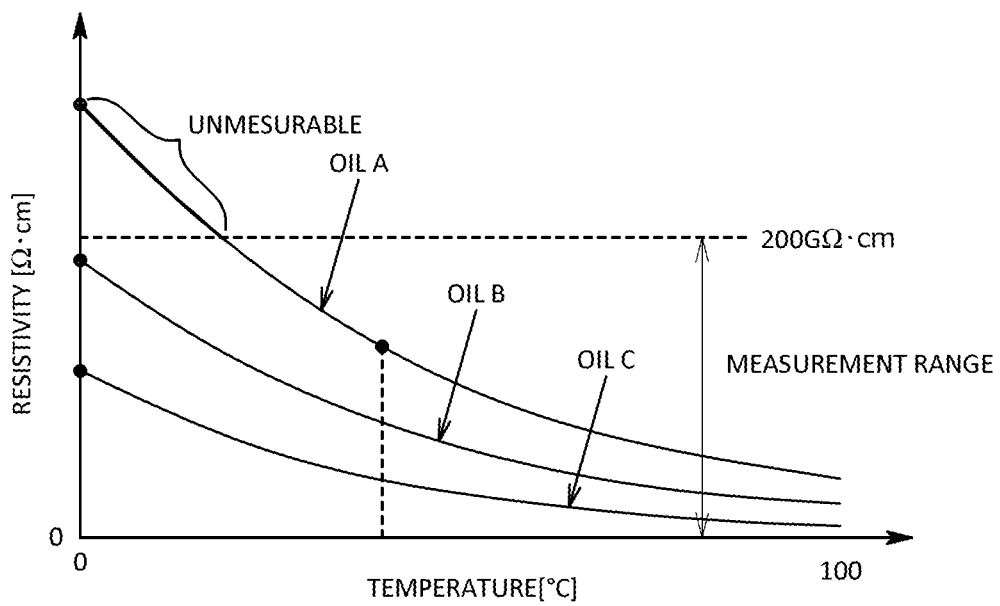
FIG. 6 is a schematic diagram illustrating the relationship between resistivities of multiple oils and temperature.

The heating temperature setting signal reception part 5 is one that receives the heating temperature setting signal indicating a heating temperature suitable to measure the resistivity of the oil contained in the oil measuring cell 2. The heating temperature setting signal is generated in such a way that a user uses input means such as a keyboard, mouse, touch panel, or temperature setting button, or a communication system of the below-described oil control system 100Z to give an input. Also, the heating temperature setting signal reception part 5 transmits the received heating temperature setting signal to the below-described heater control part 6. Note that as illustrated in FIG. 5, the resistivity of oil decreases as time passes, i.e., as the oil is deteriorated (oxidized). Also, as illustrated in FIG. 6, resistivity is different depending on a type or a temperature. In addition, the resistivity of oil exhibits a maximum before use. For this reason, heating temperatures of various oils are set so as to make resistivities of the various oils before use fall within a measurement range of the oil measuring cell 2.

The heater control part 6 acquires the heating temperature setting signal from the heating temperature setting signal reception part 5, as well as acquiring the detection signal from the temperature sensor 7 provided for the oil measuring cell 2 to compare a temperature (measured temperature) indicated by the detection signal and the temperature (setting temperature) indicated by the heating temperature setting signal, and controls current to be flowed through the heater 3 so as to make the measured temperature by the temperature sensor 7 equal to the setting temperature.

Figure 7:
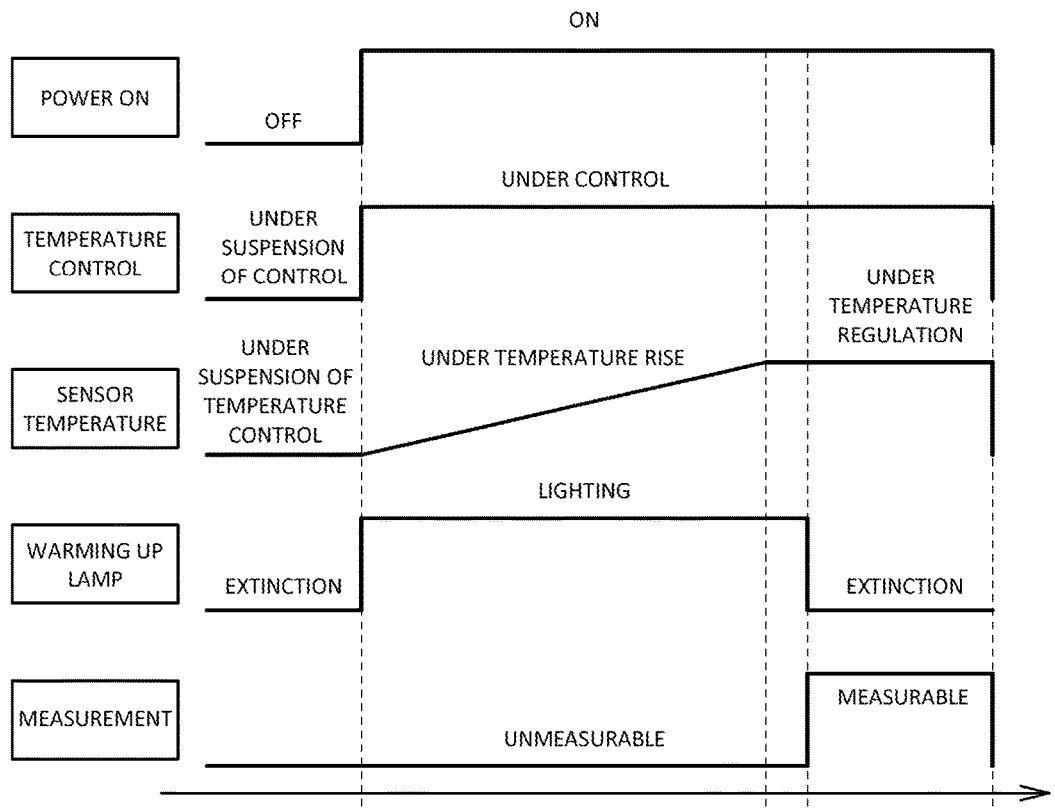
FIG. 7 is a diagram illustrating a time chart before measurement in the same embodiment.

Next, an example of a time chart before the measurement by the resistivity-measuring apparatus 100 configured as described is described with reference to FIG. 7.

First, a user powers on the resistivity-measuring apparatus 100. Then, the user uses the input means to set a heating temperature suitable to measure the resistivity of oil as a measuring target. The heating temperature setting signal indicating the heating temperature set here is acquired by the heating temperature setting signal reception part 5, and then transmitted to the heater control part 6. The heater control part 6 acquires the heating temperature setting signal to start temperature control of the heater 3. In doing so, the oil measuring cell 2 is warmed up by the heater 3. A measured temperature obtained by the temperature sensor 7 is increased toward the desired heating temperature along with the warming up by the heater 3. When the oil measuring cell 2 reaches the constant temperature after a period of the temperature increase has passed, the resistivity measuring part 4 starts to measure the resistivity of the oil.

Note that a warming up lamp provided in the control device 10 is configured to, from when the heater control part 6 starts the temperature control of the heater 3 to when the oil measuring cell 2 reaches the constant temperature, light to notify the user that the measurement is in preparation.

Also, the timing when the resistivity measuring part 4 starts the resistivity measurement may be, for example, any of the following (1), (2), and (3).

(1) The user having confirmed that the warming up lamp switched from lighting to extinction operates the input means separately provided, such as a measurement start switch, and thereby a measurement start signal is transmitted to the resistivity measuring part 4. When acquiring the measurement start signal, the resistivity measuring part 4 starts the resistivity measurement.

(2) The heater control part 6 is configured to, when determining that a measured temperature by the temperature sensor 7 and a setting temperature are the same, transmit a corresponding determination signal to the resistivity measuring part 4. When acquiring the determination signal, the resistivity measuring part 4 starts the resistivity measurement.

(3) The resistivity measuring part 4 is configured to acquire the heating temperature setting signal from the heating temperature setting signal reception part 5 or the heater control part 6, and also acquire the detection signal from the temperature sensor 7 to compare a temperature (measured temperature) indicated by the detection signal and a temperature (setting temperature) indicated by the heating temperature setting signal with each other. When determining that the measured temperature and the setting temperature are the same, the resistivity measuring part 4 starts the resistivity measurement.

(4) A computer or the like having received a signal via the below-described oil control system 100Z may be configured to perform the start of the resistivity measurement or the effectiveness determination of acquired data.

Figure 8:
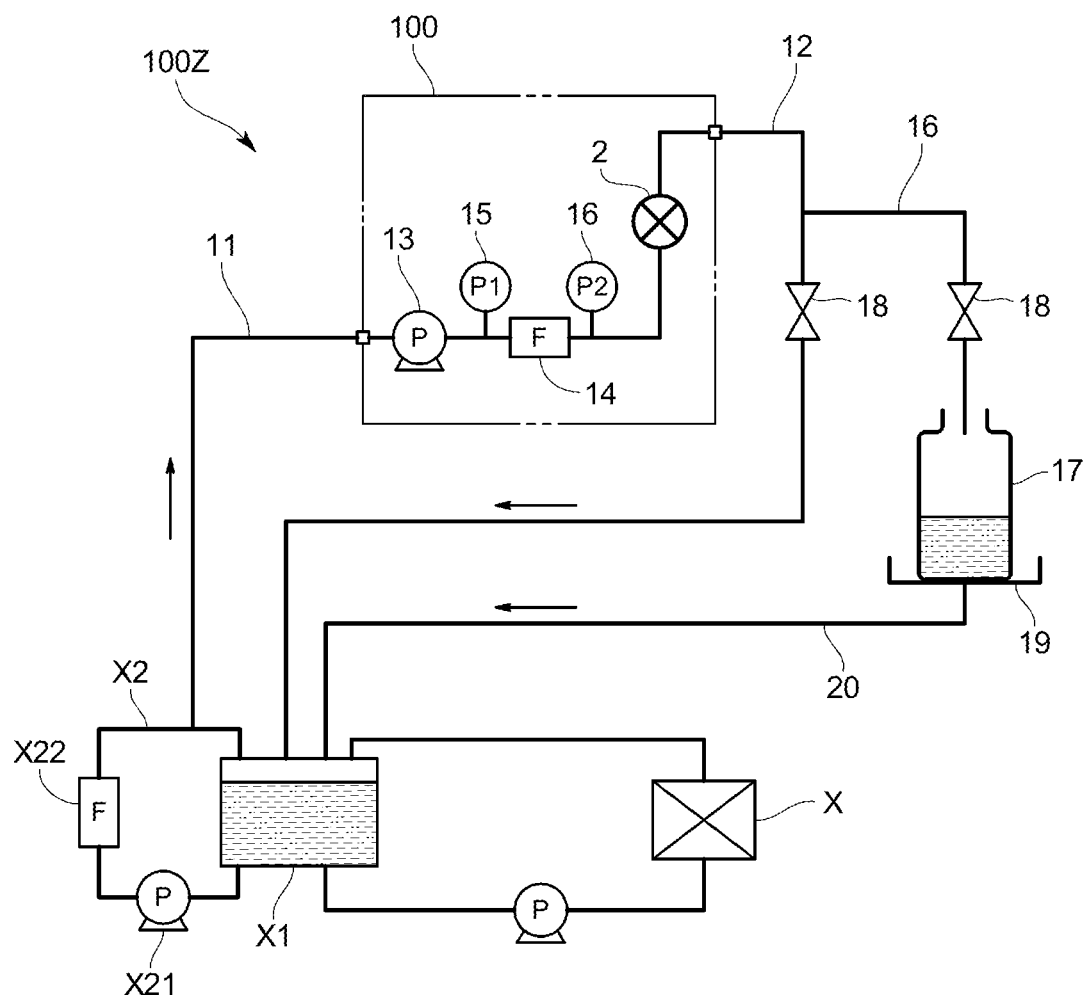
FIG. 8 is a schematic diagram illustrating an oil control system using the resistivity-measuring apparatus in the same embodiment.

Next, the oil control system 100Z using the resistivity-measuring apparatus 100 in the present embodiment is described with reference to FIG. 8. It is desirable that since the relationship among a deterioration degree, a resistivity value, and a temperature is different depending on the type of use liquid such as lubricating oil, the behavior of use liquid of a target device X controlled by the resistivity-measuring apparatus 100 is preliminarily checked by the resistivity-measuring apparatus 100, and the use liquid of which the behavior has been checked is used.

The oil control system 100Z has a transmission system (not illustrated) that automatically transmits a resistivity value and a temperature obtained by the resistivity-measuring apparatus 100 to a control apparatus (user terminal) on a controller side through a communication line, and is one that makes it possible to continuously perform oil control by acquiring the resistivity value and the temperature as signals. Note that in addition to the signals from the resistivity-measuring apparatus 100, signals from a measuring apparatus adapted to measure other measurement target items such as moisture and optical transmittance are also transmitted to the control apparatus, and therefore the control apparatus can comprehensively control the use liquid using all of the signals.

Specifically, the oil control system 100Z includes: an oil feed pipe 11 (corresponding to the above-described external pipe H1) for feeding the use liquid from a use liquid tank X1 of the target device X to the oil measuring cell 2 of the resistivity-measuring apparatus 100; and an oil return pipe 12 (corresponding to the above-described external pipe H2) for returning the oil from the oil measuring cell 2 to the use liquid tank X1. In addition, the use liquid tank X1 is provided with a purification line X2 for purifying the oil retained in the use liquid tank X1, and the purification line X2 is provided with: a pump X21 for circulating the oil through the line X2; and a filter X22 for removing foreign substances such as impurities and abrasion powder contained in the oil.

Further, an oil collecting point through an oil introduction port of the oil feed pipe 11 is the use liquid tank X1, and more specifically, on the downstream side of the filter X22 in the purification line X2. This makes it possible to feed the use liquid purified by the filter X22 to the oil measuring cell 2. Note that in the case where the purification line X2 is not provided, the oil introduction port may be provided in an area in contact with the use liquid in the use liquid tank X1.

Also, the oil feed pipe 11 is provided with a feed pump 13 for feeding the oil collected through the oil introduction port to the oil measuring cell 2. Note that the feed pump 13 may be provided in the oil return pipe 12.

Further, it is desirable that on the upstream side of the oil measuring cell 2, a foreign substance removing mechanism 14 is provided. The foreign substance removing mechanism 14 is a scavenging unit that is adapted to scavenge impurities and abrasion powder contained in the oil and includes a filter, a magnet, and the like. In addition, the scavenging unit 14 is made attachable/detachable to/from the oil feed pipe 11, and configured to be able to perform strict oil control by analyzing scavenged substances scavenged by the scavenging unit 14 taken out.

The foreign substance removing mechanism 14 in the present embodiment is a filter, on the upstream side and downstream side of which, pressure sensors 15 and 16 are provided, and configured to be able to perform filter control such as clogging of the filter 14 together with the oil control by acquiring pressures from the pressure sensors 15 and 16 as signals to use the difference between the pressures.

On the other hand, the oil return pipe 12 is provided with a sampling line 16, and thereby if a resistivity value obtained by the resistivity-measuring apparatus 100 is an abnormal value, the use liquid exhibiting the abnormal resistivity value can be sampled into a sampling container 17. Further, in the case of portably using the present system, this sampling mechanism very effectively functions because it is preferable to perform measurement on several devices using one system per day to obtain prompt results followed by performing detailed analysis using an actual sample on each of the devices and a corresponding result.

Specifically, the sampling line 16 is a sampling tube provided branching in the middle of the oil return pipe 12, and at the outlet of the sampling tube 16, the sampling container 17 is provided. Also, on the downstream side of the branching point in the oil return pipe 12 and in the sampling tube 16, selector valves 18 for switching to a tube through which the use liquid is to flow are provided. The selector valves 18 may be automatically switchable solenoid valves or manually switchable manual valves.

Further, the sampling container 17 is provided attachably/detachably to/from the sampling tube 16, and the abnormal use liquid retained in the sampling container 17 is analyzed by an analyzer such as an elemental analyzer. In addition, on the lower side of the sampling container 17, an oil pan 19 for collecting the use liquid and the like having overflowed from the sampling container 17 is provided, and the oil pan 19 is provided with a return pipe 20 for returning the collected use liquid to the use liquid tank X1.

<Effects of the Present Embodiment>

The resistivity-measuring apparatus 100 in the present embodiment configured as described applies the square wave AC voltage, and can therefore suppress the formation of electrical double layers at the boundaries between the electrodes 21 and 22 and oil to continuously measure the resistivity of the oil. Also, since the voltage in the range from 1 V to 42 V is applied, deterioration caused by the measurement, such as change in quality of the oil during the measurement, can be prevented. Note that since the AC voltage is set within the range from 1 V to 42 V, the AC power supply can be configured at low cost, and also even in case of electric shock, a risk to a human body can be reduced. Further, since the frequency is within the range from 0.5 Hz to 30 Hz, the signal outputted from the resistivity-measuring circuit C can be stabilized before switching the polarity of the AC voltage, and therefore the resistivity of the oil can be accurately measured to accurately sense the deterioration of the oil.

Also, the resistivity-measuring apparatus 100 in the present embodiment configured as described has the so-called double-sided support structure in which at the both axial direction end parts of the oil measuring cell 2, the insulating members 23 fix the inner electrode 22 with respect to the outer electrode 21, and fix the opposite distance between the inner surface of the outer electrode 21 and the outer surface of the inner electrode 22, thus suppressing a shift of the inner electrode 22 with respect to the outer electrode 21 caused by external vibration, and therefore a variation in opposite distance can be suppressed. In doing so, failed measurement due to vibration can be prevented to reduce a measurement error despite employing the structure adapted to decrease the opposite distance between the inner surface of the outer electrode 21 and the outer surface of the inner electrode 22 or the structure adapted to increase the length dimensions of the outer electrode 21 and inner electrode 22 to decrease the cell constant. As a result, measurement accuracy of electrical characteristics of the oil can be improved to accurately sense the deterioration of the oil.

Further, since the temperature of oil contained in the cell space S is regulated to a predetermined heating temperature, for each of various oils, a temperature suitable to measure the resistivity of that oil can be obtained, thus making it possible to measure resistivities of the various oils. Also, since the temperature of oil contained in the cell space S is controlled to be constant, a measurement error associated with a variation in temperature of the oil can be reduced without necessarily relying on temperature compensation, and thereby the resistivity of the oil can be accurately measured. As a result, the deterioration of various oils can be accurately sensed. Further, in the case of oil having particularly high viscosity, since the viscosity is decreased by heating, the oil can be made to easily circulate through the oil measuring cell 2, and in combination with the cell structure in the present embodiment, air bubbles can be further prevented from being accumulated.

Still further, since the resistivity-measuring apparatus 100 in the present embodiment configured as described regulates the temperature of oil contained in the cell space S to a predetermined heating temperature, for each of various oils, a temperature suitable to measure the resistivity of that oil can be obtained, thus making it possible to measure resistivities of the various oils. Also, since the temperature of oil contained in the cell space S is controlled to be constant, a measurement error associated with a variation in temperature of the oil can be reduced without necessarily relying on temperature compensation, and therefore the resistivity of the oil can be accurately measured. As a result, the deterioration of various oils can be accurately sensed. Further, in the case of oil having particularly high viscosity, the viscosity is decreased by heating, and therefore the oil can be made to easily circulate through the oil measuring cell 2.

Note that the present invention is not limited to the above-described embodiment.

For example, the resistivity-measuring apparatus 100 in the above-described embodiment may be one further having a deterioration determination part. The deterioration determination part is included in the control device 10. The deterioration determination part is one that makes a deterioration determination by comparing resistivity obtained by the resistivity measuring part 4 and a predetermined threshold value (reference resistivity) with each other. It may be configured that the reference resistivity is set for each of various oils, and for example, a user can give a setting input, or threshold data indicating a threshold value set for each of various oils is stored in a memory, and a user can select threshold data. In addition, as a deterioration determination method, besides, the deterioration determination may be made on the basis of a relationship with an initial value (resistivity) of oil being measured, for example, on the basis or a ratio to the initial value.

Also, in the case where calculated resistivity is lower than a threshold value, the deterioration determination part outputs a deterioration determination signal to a notification means control part provided in the control device 10. In addition, the notification means control part is one that controls notification means provided on the control device 10, such as a lamp and a display, to notify a user of oil deterioration.

Figure 9:
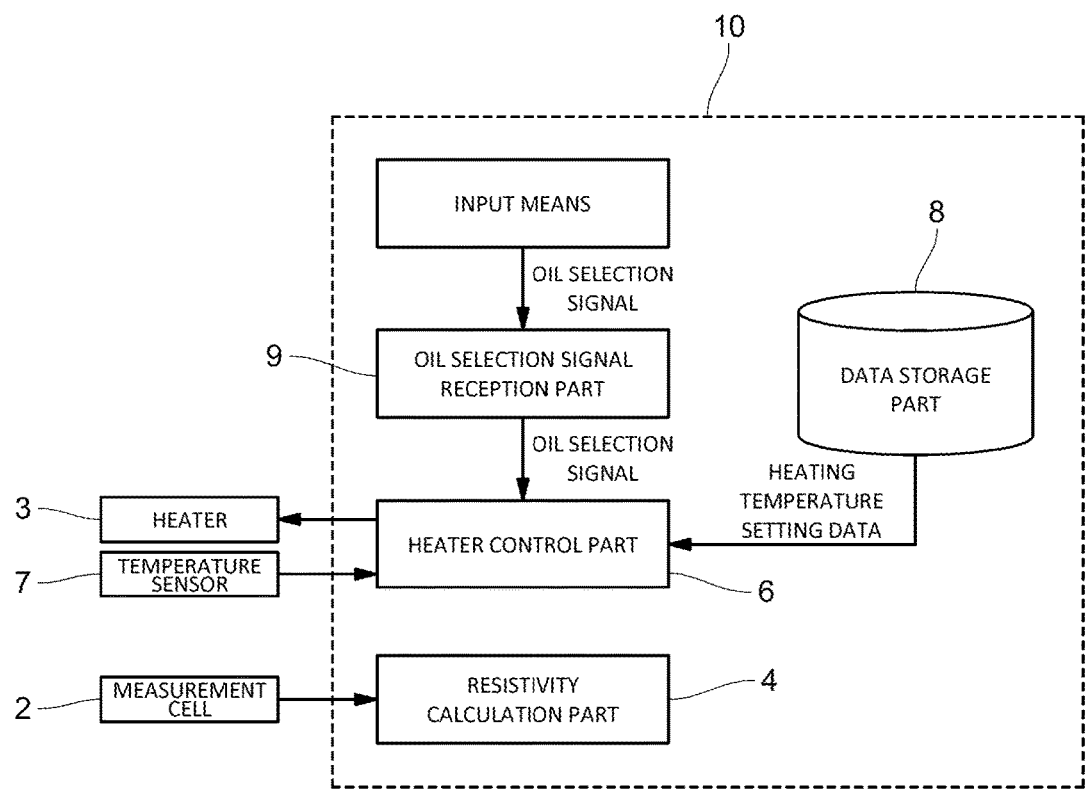
FIG. 9 is a functional configuration diagram of a control device of a resistivity-measuring apparatus in a variation.

The above-described embodiment is configured such that a user sets a heating temperature, but may be configured such that a user inputs an oil type and thereby the control device 10 side automatically sets a heating temperature. In this case, as illustrated in FIG. 9, it is possible that the control device 10 is adapted to be one including: a data storage part 8 that stores heating temperature setting data indicating a heating temperature set for each oil type; and an oil selection signal reception part 9 that receives an oil selection signal indicating the type of oil contained in the oil measuring cell 2.

The data storage part 8 is one that stores heating temperature setting data indicating a heating temperature set for each oil type. Also, heating temperature setting data is one that indicates, for example, a heating temperature set such that the resistivity of each oil before use falls within the measurement range of the oil measuring cell 2. The heating temperature setting data is preliminarily stored in the data storage part 8 by a user.

The oil selection signal reception part 9 is one that receives an oil selection signal indicating the type of oil that is contained in the oil measuring cell 2 and to be measured. The oil selection signal is generated in such a way that a user uses the input means such as a keyboard, mouse, touch panel, or oil setting button, or the communication system of the oil control system 100Z to give an input. Further, the oil selection signal reception part 9 transmits the received oil selection signal to the heater control part 6.

The heater control part 6 acquires the oil selection signal from the oil selection signal reception part 9, and on the basis of the oil selection signal and corresponding heating temperature setting data stored in the data storage part 8, sets the heating temperature (setting temperature) of the heater 3. Further, the heater control part 6 acquires a detection signal from the temperature sensor 7 provided for the oil measuring cell 2 to compare a temperature (measured temperature) indicated by the detection signal and the set heating temperature (setting temperature), and controls a value of current to be flowed through the heater 3 so as to make the temperature indicated by the detection signal of the temperature sensor 7 equal to the set heating temperature.

In such a configuration, since a user only inputs the type of oil, and thereby temperature can be regulated to a temperature suitable to measure the resistivity of the oil, a temperature suitable to measure the resistivity of each of various oils can be obtained, and therefore resistivities of the various oils can be measured in addition to the effects of the above-described embodiment.

Figure 10:
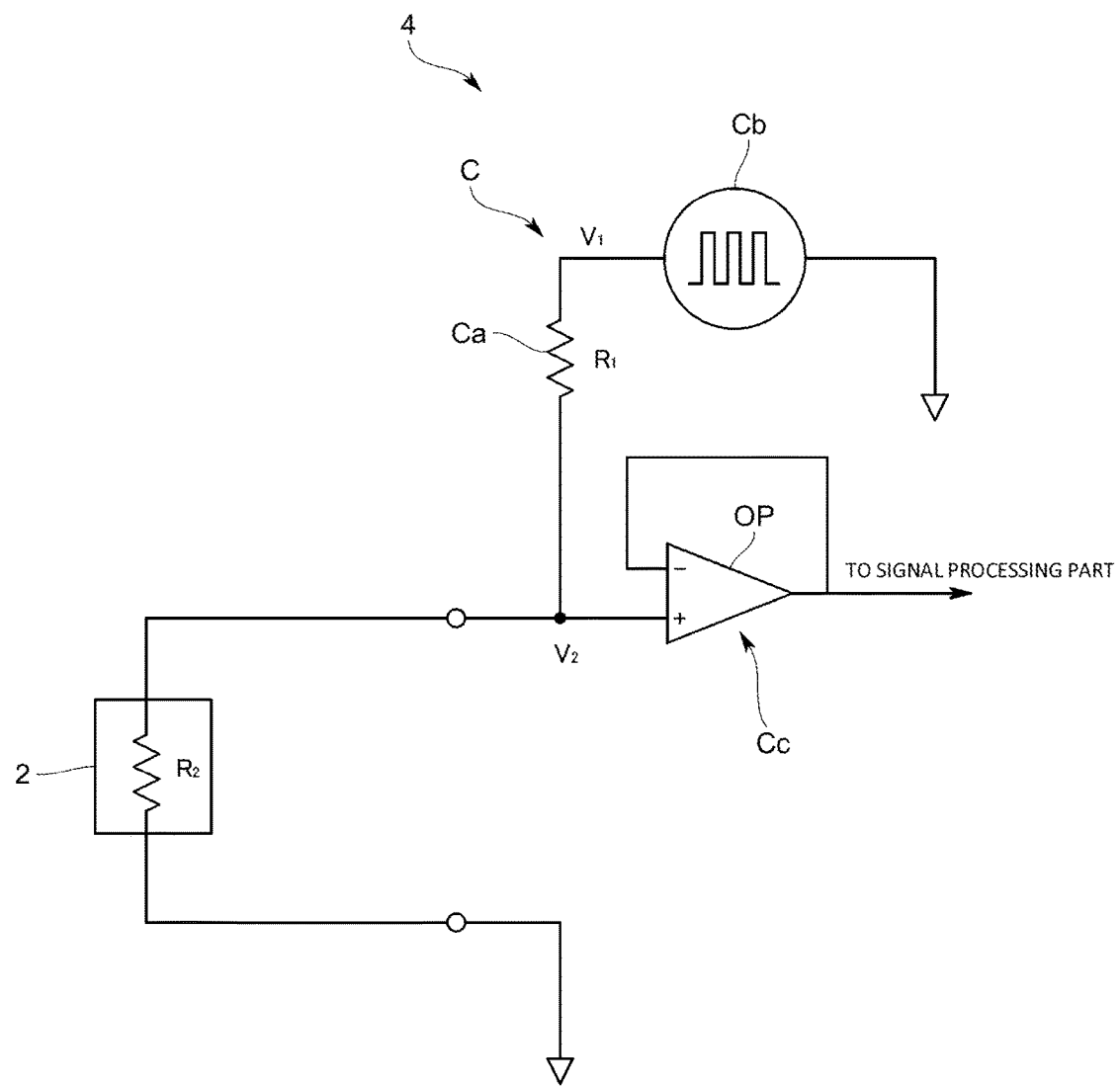
FIG. 10 is a schematic diagram illustrating a resistivity-measuring circuit in a variation.

Also, the resistivity measuring part 4 may be configured not to have the shield drive circuit C1. For example, as illustrated in FIG. 10, the resistivity measuring part 4 may be one that has the resistivity-measuring circuit C and between the outer electrode 21 and the inner electrode 22, applies the square wave AC voltage ($V_1$) having the predetermined amplitude and the predetermined frequency that makes it possible to continuously measure the resistivity of oil and prevent oil deterioration by measurement. In such a configuration, since the square wave AV voltage is applied, the formation of electric double layers at the boundaries between the electrodes 21 and 22 and the oil can be suppressed to continuously measure the resistivity of the oil. Also, since the voltage having the predetermined amplitude is applied, deterioration of the oil by measurement, such as change in quality during the measurement, can be prevented. Note that the measurement range of the resistivity measuring part 4 is 0 to 200 GΩ·cm.

Also, the above-described embodiment is configured to set a heating temperature before starting temperature control of the heater, but may be configured to, after starting temperature control of the heater or during resistivity measurement, be able to change a setting temperature set previously (e.g., before starting temperature control).

Further, instead of setting a setting temperature to a single value, it may be configured to be able to set an upper limit value and a lower limit value of heating temperature, and control the temperature of the oil measuring cell 2 between the upper limit value and the lower limit value of the heating temperature. Also, in this case, it may be configured to perform temperature compensation of resistivity calculated by the resistivity measuring part using a detected temperature obtained by the temperature sensor.

In addition, the heater in the above-described embodiment may be configured as the outer electrode or the inner electrode. That is, it may be configured to flow current through the outer electrode or the inner electrode to electrically heat the electrode, and thereby make the electrode fulfill a function as the heater. In this case, by flowing current through the inner electrode to make the inner electrode function as the heater, a liquid sample can be quickly heated to more accurately perform measurement.

Further, the oil introduction path L1 and the oil lead-out path L2 in the above-described embodiment are provided in the inner electrode 22, but may be provided in the insulating members 23.

The oil measuring cell 2 and the control device 10 may be unitized by being contained in one casing. In this case, it is possible to provide the casing with a handle for carrying to configure the casing as a portable one. Also, it is possible to provide the casing with: a feed port that is connected with a pipe for feeding oil of an external bearing, hydraulic system, or the like to the oil measuring cell; and a discharge port that is connected with a pipe for discharging the oil after measurement from the oil measuring cell to the outside or for returning the oil after measurement to the external bearing, hydraulic system, or the like.

In addition, the above-described embodiment detects voltage ($V_2$) between the outer electrode 21 and the inner electrode 22 to calculate resistivity, but may be adapted to detect voltage applied across the reference resistor Ca to calculate resistivity. In this case, the resistance value $R_1$ of the reference resistor Ca is detected using a differential circuit.

Further, in the above-described embodiment, as an oil analyzer, the resistivity-measuring apparatus adapted to measure the resistivity of oil is described; however, besides, the oil analyzer may be one adapted to measure another electrical characteristic of the oil such as oxidation-reduction potential or a dielectric constant.

Still further, in the above-described embodiment, the oil measuring cell has an oil heating function and the outer electrode is provided with the heater; however, the oil measuring cell may be configured to be one not having an oil heating function. In this case, it may be configured that the outer electrode is not provided with a heater.

Yet further, the heater in the above-described embodiment may be configured as the outer electrode or the inner electrode. That is, it may be configured to flow current through the outer electrode or the inner electrode to electrically heat the electrode, and thereby make the electrode fulfill a function as the heater. In this case, by flowing current through the inner electrode to make the inner electrode function as the heater, a liquid sample can be quickly heated to more accurately perform measurement.

Besides, it should be appreciated that the present invention is not limited to any of the above-described embodiment, but can be variously modified without departing from the scope thereof.

INDUSTRIAL APPLICABILITY

According to the present invention, the resistivity of a liquid sample can be continuously measured with accuracy, and also the deterioration of the liquid sample associated with measurement, such as change in quality, can be prevented.

The invention claimed is:

1. A resistivity-measuring circuit that measures resistivity in order to sense deterioration of a liquid sample, the resistivity-measuring circuit
   being one that measures the resistivity of the liquid sample between a pair of electrodes comprising a first electrode and a second electrode by detecting voltage generated between the first electrode and the second electrode, the first electrode being connected to a first wiring line and the second electrode being connected to a second wiring line,
   having a shield drive circuit having a conductor which at least partially covers at least one of the first wiring line and the second wiring line without contacting with portions of the first wiring line or the second wiring line that are partially covered by the conductor, wherein the conductor is connected to an operational amplifier, the shield drive circuit zeroing a potential difference of floating capacitance formed between the first and second wiring lines at the portions of the respective first and second wiring lines that are partially covered by the conductor, and
   between the pair of electrodes, applying square wave AC voltage having an amplitude of 1 V to 42 V and a frequency of 0.5 Hz to 30 Hz.

2. A resistivity-measuring apparatus having the resistivity-measuring circuit according to claim 1.

3. A liquid sample control method that continuously performs liquid sample control by using the resistivity-measuring apparatus according to claim 2 to acquire a resistivity value and temperature as signals.

4. A liquid sample control system comprising:
a transmission system that automatically transmits the resistivity value and the temperature acquired as the signals for the liquid sample control method according to claim 3 to a controller side through a communication line; and
a feed pump for feeding the liquid sample to a measuring cell having the pair of electrodes.

5. The liquid sample control system according to claim 4, wherein
the feed pump is provided in at least one of a feed pipe for feeding the liquid sample to the measuring cell, and a discharge pipe for discharging the liquid sample from the measuring cell for the liquid sample.

6. The liquid sample control system according to claim 4, wherein
a signal or data is inputted to the resistivity-measuring apparatus via a communication system.

7. The liquid sample control system according to claim 5, wherein the feed pipe for feeding the liquid sample to the measuring cell is provided with a foreign substance removing mechanism.

8. The liquid sample control method using the liquid sample control system according to claim 7, wherein
the foreign substance removing mechanism is a filter, and the liquid sample control method performs filter control as well as the liquid sample control by providing a pressure sensor at least on an upstream side of the filter to acquire pressure from the pressure sensor as a signal.

* * * * *